(12) United States Patent
Blatter et al.

(10) Patent No.: US 7,932,387 B2
(45) Date of Patent: Apr. 26, 2011

(54) CRYSTALLINE FORMS OF ROSUVASTATIN CALCIUM SALT

(75) Inventors: Fritz Blatter, Reinach (CH); Paul Adriaan Van Der Schaaf, Hagenthal-le-Haut (FR); Martin Szelagiewicz, Münchenstein (CH)

(73) Assignee: BASF SE, Ludwigshafen (DE)

( * ) Notice: Subject to any disclaimer, the term of this patent is extended or adjusted under 35 U.S.C. 154(b) by 808 days.

(21) Appl. No.: 11/883,008

(22) PCT Filed: Jan. 23, 2006

(86) PCT No.: PCT/EP2006/050351
§ 371 (c)(1),
(2), (4) Date: Jul. 25, 2007

(87) PCT Pub. No.: WO2006/079611
PCT Pub. Date: Aug. 3, 2006

(65) Prior Publication Data
US 2008/0194604 A1    Aug. 14, 2008

(30) Foreign Application Priority Data

Jan. 31, 2005    (EP) .................................... 05100598

(51) Int. Cl.
*C07D 239/42*    (2006.01)
*A61K 31/505*    (2006.01)
*A61P 3/06*    (2006.01)

(52) U.S. Cl. ......... 544/332; 544/330; 544/297; 514/275

(58) Field of Classification Search ................... 544/297, 544/330, 332
See application file for complete search history.

(56) References Cited

U.S. PATENT DOCUMENTS

| | | | |
|---|---|---|---|
| 5,260,440 A | 11/1993 | Hirai et al. ...................... | 544/322 |
| 6,589,959 B1 * | 7/2003 | Taylor ............................ | 514/275 |
| 6,777,552 B2 * | 8/2004 | Niddam-Hildesheim et al. ............................. | 544/332 |
| 7,511,140 B2 * | 3/2009 | Horbury et al. ................ | 544/297 |
| 2006/0142582 A1 | 6/2006 | Van Der Schaaf et al. ... | 546/177 |
| 2006/0241167 A1 | 10/2006 | Van Der Schaaf et al. ... | 514/415 |
| 2007/0173536 A1 | 7/2007 | Van Der Schaaf et al. ... | 514/376 |
| 2008/0176878 A1 | 7/2008 | Wizel et al. | |

FOREIGN PATENT DOCUMENTS

| | | |
|---|---|---|
| WO | 2005/077916 | 8/2005 |
| WO | 2006/035277 | 4/2006 |

OTHER PUBLICATIONS

Iida et al., FEBS Letters 520, 177-181, 2002.*
Rutishauser Swiss Medical Weekly, 126, 41-49, 2006.*
Khan et al., Diabetes Care 25(4), 708-7VI, 2002.*

* cited by examiner

*Primary Examiner* — Venkataraman Balasubramanian
(74) *Attorney, Agent, or Firm* — Shiela A. Loggins

(57) ABSTRACT

Bis[(E)-7-[4-(4-fluorophenyl)-6-isopropyl-2-[methyl(methylsulfonyl)amino]pyrimidin-5-yl]-(3R,5S)-3,5-dihydroxyhept-6-enoic acid] (also known as rosuvastatin) calcium salt and hydrates can exist in new crystal forms B and C. These crystal forms provide a higher diversity on crystalline materials to optimize manufacture, formulation and biological efficiency.

9 Claims, 1 Drawing Sheet

CRYSTALLINE FORMS OF ROSUVASTATIN CALCIUM SALT

FIELD OF THE INVENTION

The present invention relates to crystalline forms of rosuvastatin calcium. This invention also relates to processes for preparing crystalline forms of rosuvastatin calcium. This invention also relates to compositions comprising of crystalline forms of rosuvastatin calcium and a pharmaceutically acceptable carrier, and to methods of using crystalline forms of rosuvastatin calcium and compositions thereof to treat a disease condition wherein inhibition of HMG CoA reductase is beneficial.

BACKGROUND TO THE INVENTION

Rosuvastatin calcium is known by its chemical name as bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt of formulae (1)

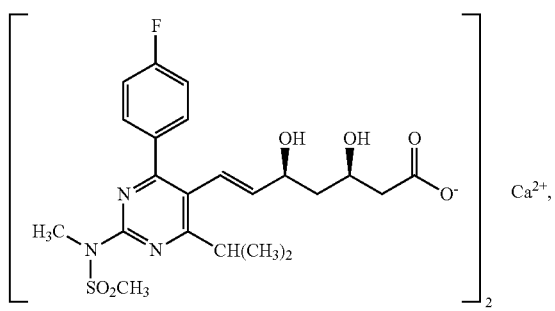

(1)

which is known to inhibit the HMG-CoA reductase, and subsequently suppress the biosynthesis of cholesterol. Rosuvastatin calcium is useful in the treatment of hypercholesterolemia, hyperlipoproteinemia, and atherosclerosis. Rosuvastatin calcium may form hydrates with a varying content of water.

EP-A1-0 521 471 describes in example 7 the preparation of rosuvastatin calcium in powder form. Rosuvastatin sodium is dissolved in water at room temperature and an aqueous calcium chloride solution is added dropwise. The collected precipitate is an amorphous powder. U.S. Pat. No. 6,777,552 discloses the preparation of rosuvastatin calcium through hydrolysation of methyl 7-[4-(4-fluorophenyl)-6-isopropyl-2-[methyl(methylsulfonyl)amino]pyrimidin-5-yl]-(3R,5S)-3,5-dihydroxy-(E)-6-heptanoate with calcium hydroxide in a water/ethanol solution. The compound is not isolated from the solution to characterize an amorphous or crystalline state.

In WO 00/42024 is disclosed a crystalline form, hereafter referred to as form A of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof, which are prepared by dissolving the amorphous form in a mixture of water and an organic solvent such as acetone or acetonitrile under heating and then cooling the solution to precipitate crystalline form A.

Crystalline forms often show desired different physical and/or biological characteristics which may assist in the manufacture or formulation of the active compound, to the purity levels and uniformity required for regulatory approval. Crystalline forms of such active compounds may also possess improved pharmacological characteristics, for example, improved bioavailability, and therefore, novel crystalline forms offer enhanced possibilities to modulate and design improved drug products. There exists therefore a need for other crystal forms than form A of bis[(E)-7-[4-(4-fluorophenyl)-6-isopropyl-2-[methyl(methylsulfonyl)amino]pyrimidin-5-yl]-(3R,5S)-3,5-dihydroxyhept-6-enoic acid] calcium salt to have a sufficient diversity on crystalline materials to optimize manufacture, formulation and biological efficiency.

SUMMARY OF THE INVENTION

This invention provides crystalline forms B and C of rosuvastatin calcium and processes for their manufacture.

A first object of the invention is a crystalline form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof which exhibits a characteristic X-ray powder diffraction pattern with characteristic peaks expressed in d-values (Å:
30.00 (vs), 18.10 (m), 15.00 (m) and 10.00 (m);
hereinafter designated as form B.

More specifically, the present invention comprises a crystalline form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof, which exhibits a characteristic X-ray powder diffraction pattern with characteristic peaks expressed in d-values (Å):
30.0 (vs); 18.1 (m); 15.0 (m); 12.9 (w); 10.7 (vw); 10.0 (m); 9.5 (w); 8.6 (vs); 7.7 (w); 6.3 (vw); 6.00 (vw); 5.56 (vw); 4.74 (w); 4.57 (w); 4.34 (vw); 4.24 (vw); 4.02 (vw); 3.87 (w); 3.79 (w); and 3.66 (vw); hereinafter designated as form B.

Here and in the following the abbreviations in brackets mean: (vvs)=very very strong intensity; (vs)=very strong intensity; (s)=strong intensity; (m)=medium intensity; (w)=weak intensity and (vw)=very weak intensity.

In still another preferred embodiment, the present invention comprises a crystalline form B of bis[(E)-7-[4-(4-fluorophenyl)-6-isopropyl-2-[methyl(methylsulfonyl)amino]pyrimidin-5-yl]-(3R,5S)-3,5-dihydroxyhept-6-enoic acid] calcium salt and hydrates thereof, which exhibits characteristic X-ray powder diffraction patterns as exhibited in FIG. 1.

A second object of the invention is a process for the preparation of crystalline form B of bis-[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof which comprises
  a) dissolving at ambient temperature a rosuvastatin calcium or a hydrate thereof in water containing an anionic surfactant;
  b) removing at ambient temperature water to reduce the volume of water to at least 30% of the volume used to dissolve rosuvastatin;
  c) stirring the obtained suspension at ambient temperature for a time sufficient to produce said form B; and
  d) filtering off the solid.

The concentration of rosuvastatin in water may range from 0.001 to 1 percent by weight, and preferably from 0.01 to 0.8 percent by weight.

Ambient temperature means in the context of the invention a temperature range at room temperature, comprising 20 to 30° C. and preferably about 23 to 26° C.

Anionic surfactants are well known and may comprise organic compounds having hydrophilic acidic groups and hydrophobic carbon residues with for example 6 to 30 and preferably 10 to 22 carbon atoms, and optionally hetero atoms such as oxygen. Examples for acidic groups are —$CO_2H$, —$SO_3H$, —$OSO_3H$ and —$PO_3H$. Examples for carbon residues are $C_8$-$C_{22}$alkyl and $C_6$-$C_{18}$alkylphenyl. The anionic surfactants may be used in the form of salts such as sodium or potassium salts. Preferred anionic surfactants are alkyl sulphates having for example formula $C_8$-$C_{22}$alkyl$OSO_3H$ and their sodium or potassium salts. Particularly preferred are alkyl sulphates having formula $C_{10}$-$C_{18}$alkyl$OSO_3H$ and their sodium or potassium salts. The amount of used anionic surfactant may range from 0.001 to 0.5 percent by weight and preferably 0.01 to 0.2 percent by weight, referred to the amount of water.

Removal of water may be carried out applying vacuum, a flow of inert gas such as nitrogen or air, or both. The volume reduction is preferably 50%, more preferably 65% and especially preferred 80% or more.

Phase equilibration in process step c) may be carried out for a time period of hours to several days, e.g. 4 hours to 20 days or 8 hours to 10 days.

Crystal form B is isolated after process step c) by filtering off the crystals, which may be washed then with a small amount of water and dried then, e.g. in vacuum, an inert gas flow or both at ambient temperature.

Form B can be dried below 80° C., and is obtained as a fine powder with typical particle size distributions with the median size between 1 and 50 μm, preferably between 1 to 10 μm. This particle size range ensures a fast dissolution profile, while retaining the favourable handling properties in the formulation process. Form B is better soluble in water and in physiological liquids than form A but chemically and physically more stable than the amorphous form.

A third object of the invention is a crystalline form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof which exhibits a characteristic X-ray powder diffraction pattern with characteristic peaks expressed in d-values (Å) peak expressed in 2θ-values (Å), measure with a conventional powder X-ray diffractometer using Cu—Kα radiation at 2θ=3.6°±2° (m):
hereinafter designated as form C.

In a further embodiment, the present invention comprises a crystalline form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof, which exhibits characteristic X-ray powder diffraction peaks expressed in 2θ-values (Å), measured with a conventional powder X-ray diffractometer using Cu—Kα radiation at
2θ=3.6°±2° (m) and at 2θ=19°±5° (m, broad)
hereinafter designated as form C.

In a preferred embodiment, the present invention comprises a crystalline form C of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof, which exhibits characteristic X-ray powder diffraction patterns as exhibited in FIG. 2.

It was surprisingly found that crystal form C can be prepared by phase equilibration starting with suspended amorphous rosuvastatin calcium or a hydrate thereof in an organic solvent containing a small amount of water. The organic solvent preferably provides a low solubility for the amorphous rosuvastatin calcium or a hydrate thereof, which may be in the range of 0.01 to 10 mg/ml, more preferably 0.1 to 5 mg/ml and particularly 0.1 to 3 mg/ml.

A fourth object of the invention is a process for the preparation of crystalline form C of bis-[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof which comprises
    a) suspending at ambient temperature an amorphous rosuvastatin calcium or a hydrate thereof in an organic solvent which has a low solubility for said rosuvastatin calcium or a hydrate thereof and which contains a small amount of water;
    b) heating the suspension to a temperature of at least 40° C. for a short time period;
    c) cooling down thereafter the suspension to a temperature below 20° C.;
    d) stirring the suspension at the temperature of step c) for a time period of up to 4 days;
    e) raising the temperature to ambient temperature and stirring for a time period sufficient to form crystal form C at ambient temperature; and
    f) filtering off afterwards the crystalline solid from the suspension.

Organic solvents which have a low solubility may be selected from aliphatic alcohols, having at least 2 carbon atoms and up to 12, preferably up to 6 carbon atoms, such as ethanol, n- or i-propanol, n-, i- or t-butanol, pentanols, hexanols, octanols, decanols and dodecanols. Organic solvents which have a low solubility may also be selected from aliphatic or cycloaliphatic hydrocarbons such as pentane, hexane, heptane, octane, petrolether, cyclohexane and methylcyclohexane. Organic solvents which have a low solubility may further be selected from aliphatic non-cyclic ethers such as diethylether, di-n- or -i-propylether, di-n-, -i- or t-butylether, methyl-propylether, methyl-n-butylether and methyl-t-butylether. Some preferred solvents are $C_2$-$C_4$alkanols, $C_5$-$C_8$alkanes, $C_6$-$C_8$cycloalkanes, di-i-propylether and methyl-t-butylether.

Small amount of water means in the context of the invention a content of 0.01 to 20, preferably 0.1 to 10 and in particular 0.1 to 3 volume percent.

The suspension may be heated in process step b) to a temperature of at least 40° C. and up to 120° C., preferably to 50° C. to 100° C., and particularly 60° C. to 90° C.

Short time period in process step b) may mean at least for 2 minutes and up to 30 minutes, preferably up to 20 minutes and most preferably up to 5 to 10 minutes.

The suspension may be cooled in process step c) to preferably −20° C. to 15° C. and more preferably −10° C. to 10° C.

The time period in process step may be for example from 12 hours up to 4 days, preferably 24 hours to 72 hours.

The time period sufficient to form crystal form C may range from 10 to 150 hours, preferably 24 to 120 hours.

Crystal form C is isolated after process step e) by filtering off the crystals, which may be washed then with a small amount of water and dried then, e.g. in vacuum, an inert gas flow or both at ambient temperature.

Form C can be dried below 80° C., and is obtained as a fine powder with typical particle size distributions with the median size between 1 and 50 μm, preferably between 1 to 10 μm. This particle size range ensures a fast dissolution profile, while retaining the favourable handling properties in the formulation process. Form C is better soluble in water and in physiological liquids than form A but chemically and physically more stable than the amorphous form.

The crystal forms B and C may be used in pharmaceutical compositions and additionally as intermediates and starting materials to produce the thermodynamically most stable form A.

Accordingly, this invention is also directed to a pharmaceutical composition comprising the crystal forms B and/or C of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof, and a pharmaceutically acceptable carrier or diluent.

The amount of crystal forms of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof substantially depends on type of formulation and desired dosages during administration time periods. The amount in an oral formulation may be from 0.1 to 200 mg, preferably from 0.5 to 100 mg, and more preferably from 1 to 50 mg.

Oral formulations may be solid formulations such as capsules, tablets, pills and troches, or liquid formulations such as aqueous suspensions, elixirs and syrups. Solid and liquid formulations encompass also incorporation of the crystal forms B and/or C of into liquid or solid food.

The crystal forms according to the invention may be directly used as powders (micronized particles), granules, suspensions or solutions, or they may be combined together with other pharmaceutically acceptable ingredients in admixing the components and optionally finely divide them, and then filling capsules, composed for example from hard or soft gelatine, compressing tablets, pills or troches, or suspend or dissolve them in carriers for suspensions, elixirs and syrups. Coatings may be applied after compression to form pills.

Pharmaceutically acceptable ingredients are well known for the various types of formulation and may be for example binders such as natural or synthetic polymers, excipients, lubricants, surfactants, sweetening and flavouring agents, coating materials, preservatives, dyes, thickeners, adjuvants, antimicrobial agents and carriers for the various formulation types.

Examples for binders are gum tragacanth, acacia, starch, gelatine, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyesterpolyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated poly-acrylamides, poly-maleic acid and esters or -amides thereof, poly-acrylic acid and esters or amides thereof, poly-vinylalcohol und esters or -ethers thereof, poly-vinylimidazole, poly-ylnylpyrrolidon, und natural polymers like chitosan, carragenan or hyaluronic aid.

Examples for excipients are phosphates such as dicalcium phosphate.

Examples for lubricants are natural or synthetic oils, fats, waxes, or fatty acid salts like magnesium stearate.

Surfactants may be anionic, anionic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials gelatine, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for liquid carriers are water, alcohols such as ethanol, glycerol, propylene glycol, liquid polyethylene glycols, triacetin and oils. Examples for solid carriers are talc, clay, microcrystalline cellulose, silica, alumina and the like.

The formulation according to the invention may also contain isotonic agents, such as sugars, buffers or sodium chloride.

The crystal forms according to the invention may also be formulated as effervescent tablet or powder, which disintegrate in an aqueous environment to provide a drinking solution.

A syrup or elixir may contain the polymorph of the invention, sucrose or fructose as sweetening agent a preservative like methylparaben, a dye and a flavouring agent.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well-known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of Rosuvastatin calcium whereupon the properties that distinguish the solid forms of Rosuvastatin calcium are lost. However, the use of the novel forms to prepare such solutions is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents.

A coated tablet may have a coating on the surface of the tablet or may be a tablet comprising a powder or granules with an enteric-coating.

Slow release formulations may also be prepared from the crystal form according to the invention in order to achieve a controlled release of the active agent in contact with the body fluids in the gastro intestinal tract, and to provide a substantial constant and effective level of the active agent in the blood plasma. The crystal forms may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The crystal forms of the invention are also useful for administering a combination of therapeutic effective agents to an animal. Such a combination therapy can be carried out in using at least one further therapeutic agent which can be additionally dispersed or dissolved in a formulation.

The crystal forms of this invention and its formulations respectively can be also administered in combination with other therapeutic agents that are effective to treat a given condition to provide a combination therapy.

The crystal forms and the pharmaceutical composition according to the invention are highly suitable for effective treatment of disorders in connection with need of inhibiting the HMG-CoA reductase, and subsequently suppressing the biosynthesis of cholesterol. Crystalline forms B and C of Rosuvastatin calcium and hydrates thereof and pharmaceutical composition are useful in the treatment of hypercholesterolemia, hyperlipoproteinemia, and atherosclerosis.

An object of the invention is also a therapeutic method for producing an HMG-CoA reductase inhibiting effect in a mammal comprising administering to a mammal in need of such therapy, an effective amount of a crystal form B and/or C of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof.

The polymorphic forms of the invention may be used as single component or as mixtures with other solid forms, which may be crystalline or amorphous.

As to the novel polymorphic forms of Rosuvastatin calcium it is preferred that these contain 25-100% by weight, especially 50-100% by weight, of at least one of the novel forms, based on the total amount of Rosuvastatin calcium. Preferably, such an amount of the novel polymorphic forms of Rosuvastatin calcium is 75-100% by weight, especially 90-100% by weight. Highly preferred is an amount of 95-100% by weight.

Another object of the invention is a method of delivering a crystal form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof to a host, comprising administering to a host an effective amount of a crystal form B and/or C according to the invention.

A further object of the invention is the use of a crystal form B and/or C of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof for the manufacture of a medicament useful in the treatment of disorders in connection with need of inhibiting the HMG-CoA reductase, and subsequently suppressing the biosynthesis of cholesterol, and especially useful in the treatment of hypercholesterolemia, hyperlipoproteinemia, and atherosclerosisin in a mammal, such as a human; and crystal forms B and/or C according to the invention for use in medical therapy.

The following examples illustrate the invention.
A) Preparation of Crystalline Forms B and C

EXAMPLE A1

Preparation of Crystal Form B 79 mg amorphous rosuvastatin calcium are dissolved in 20 ml of bi-distilled water containing 10 mg of sodium dodecyl sulphate. The volume of the solution is reduced then to about 3 ml under a nitrogen gas flow of about 30 ml/min. The resulting suspension is stirred thereafter at 23±2° C. The crystals are filtered off, washed with 2 ml bi-distilled water and then dried in air at room temperature. The dried crystalline solid is investigated by powder X-ray diffraction and it shows a diffraction pattern as displayed in FIG. 1.

EXAMPLE A2

Preparation of Crystal Form C 49 mg amorphous rosuvastatin calcium are suspended in 3 ml t-butyl-methylether, which is saturated with water. The suspension is heated to 75° C. for a few minutes and then cooled to 5° C. The resulting suspension is stirred for 48 hours at 5° C. The temperature is thereafter raised to 23±2° C. and stirring of the suspension is continued at this temperature for 5 days. The formed white solid is filtered off, dried in air at ambient temperature and then dried in air for about 2 hours. The dried crystalline solid is investigated by powder X-ray diffraction and it shows a diffraction pattern as displayed in FIG. 2.

Experimental

Powder X-ray Diffraction (PXRD): PXRD is performed on a Philips 1710 powder X-ray diffractometer using CuK$_\alpha$ radiation. D-spacings are calculated from the 2θ values using the wavelength of 1.54060 Å. Generally, 2θ values are within an error of ±0.1-0.2°. The experimental error on the d-spacing values is therefore dependent on the peak location.

Figure 1:
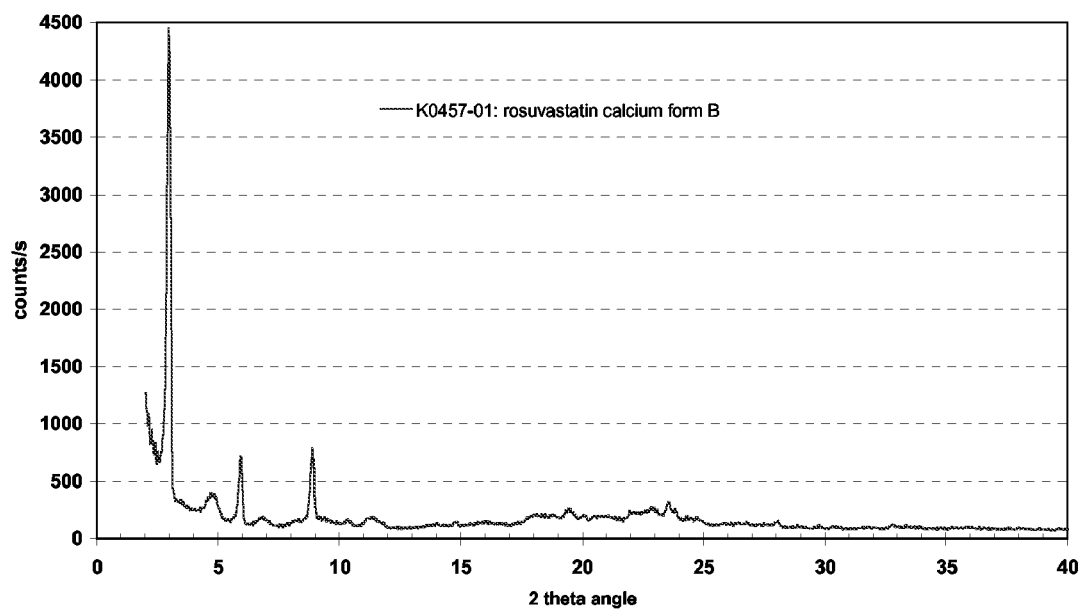
FIG. 1 is a characteristic X-ray powder diffraction pattern of form B
Figure 2:
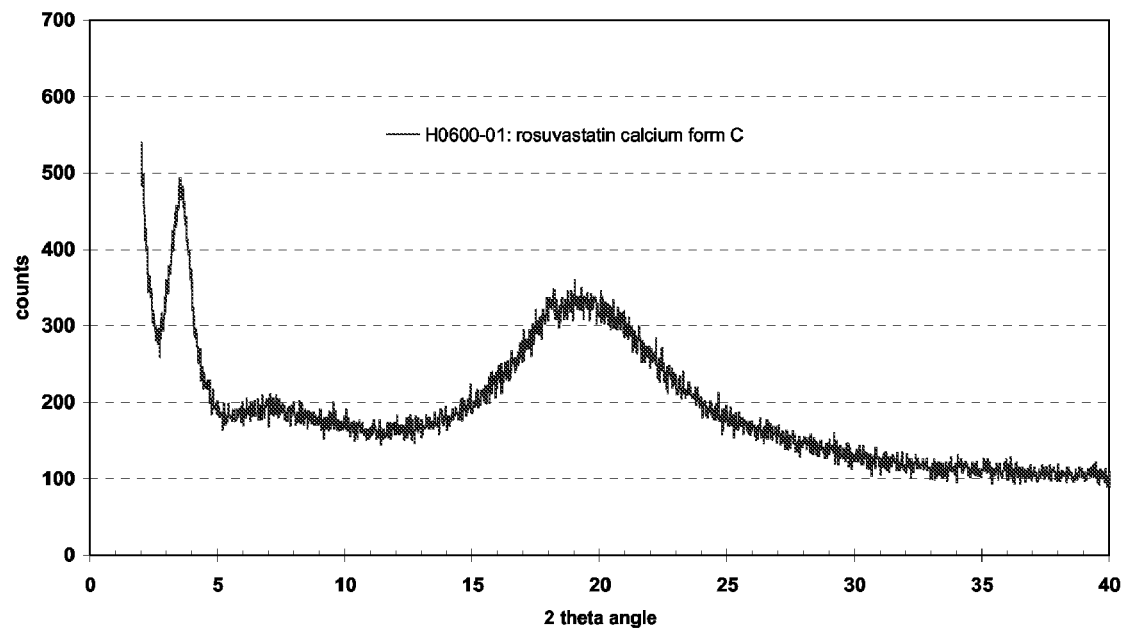
FIG. 2 is a characteristic X-ray powder diffraction pattern of form C

The invention claimed is:

1. A crystalline hydrate form of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt which exhibits a characteristic X-ray powder diffraction pattern with characteristic peaks expressed in d-values (Å):
   18.1 (m); 12.9 (w); 10.7 (vw); 9.5 (w); 8.6 (vs); 7.7 (w); 6.3 (vw); 5.56 (vw); 4.74 (w); 4.57 (w);
   4.34 (vw); 4.24 (vw); 4.02 (vw); 3.87 (w); and 3.66 (vw); hereinafter designated as form B.

2. A process for the preparation of crystalline form B of bis[(E)-7-[4-(4-fluorophenyl)-6-isopropyl-2-[methyl(methylsulfonyl)amino]pyrimidin-5-yl](3R,5S)-3,5-dihydroxyhept-6-enoic acid] calcium salt and hydrates thereof according to claim 1, which comprises a) dissolving at ambient temperature a rosuvastatin calcium or a hydrate thereof in water containing an anionic surfactant;
b) removing water at ambient temperature to reduce the volume of water by 30% or more, relative to the volume used to dissolve rosuvastatin;
c) stirring the obtained suspension at ambient temperature for a time sufficient to produce said form B; and
d) filtering off the solid.

3. A process according to claim 2, wherein the concentration of rosuvastatin in water in step a) ranges from 0.001 to 1 percent by weight.

4. A process according to claim 2, wherein ambient temperature means a temperature range at room temperature, comprising 20 to 30° C.

5. A process according to claim 2, wherein the anionic surfactant comprises organic compounds having hydrophilic acidic groups and hydrophobic carbon residues with 6 to 30 carbon atoms, and optionally hetero atoms such as oxygen, and salts thereof.

6. A process according to claim 5, wherein the anionic surfactant comprises alkyl sulphates.

7. A process according to claim 6, wherein the anionic surfactant comprises alkyl sulphates having formula $C_8$-$C_{22}$alkylOSO$_3$H.

8. A process according to claim 2, wherein the amount of anionic surfactant ranges from 0.001 to 0.5 percent by weight, relative to the amount of water.

9. A process according to claim 2, wherein the phase equilibration in process step c) is carried out for a time period of hours to several days.

* * * * *